United States Patent
Weiner et al.

(10) Patent No.: US 11,179,458 B2
(45) Date of Patent: Nov. 23, 2021

(54) IMMUNOGENICITY OF AN OPTIMIZED SYNTHETIC CONSENSUS DNA VACCINE FOR PORCINE EPIDEMIC DIARRHEA VIRUS

(71) Applicant: The Trustees of the University of Pennsylvania, Philadelphia, PA (US)

(72) Inventors: David Weiner, Merion, PA (US); Emma L. Reuschel, Philadelphia, PA (US); Karuppiah Muthumani, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 822 days.

(21) Appl. No.: 15/545,409

(22) PCT Filed: Jan. 22, 2016

(86) PCT No.: PCT/US2016/014553
§ 371 (c)(1),
(2) Date: Jul. 21, 2017

(87) PCT Pub. No.: WO2016/118880
PCT Pub. Date: Jul. 28, 2016

(65) Prior Publication Data
US 2018/0000928 A1  Jan. 4, 2018

Related U.S. Application Data

(60) Provisional application No. 62/107,165, filed on Jan. 23, 2015.

(51) Int. Cl.
| | | |
|---|---|---|
| *A61K 39/215* | (2006.01) | |
| *A61N 1/32* | (2006.01) | |
| *C12N 7/00* | (2006.01) | |
| *C07K 14/005* | (2006.01) | |
| *A61K 35/12* | (2015.01) | |
| *A61K 39/00* | (2006.01) | |

(52) U.S. Cl.
CPC ........... *A61K 39/215* (2013.01); *A61K 35/12* (2013.01); *A61N 1/327* (2013.01); *C07K 14/005* (2013.01); *C12N 7/00* (2013.01); *A61K 2039/5256* (2013.01); *A61K 2039/53* (2013.01); *A61K 2039/54* (2013.01); *A61K 2039/575* (2013.01); *C12N 2770/20034* (2013.01); *C12N 2770/20071* (2013.01)

(58) Field of Classification Search
CPC .............. A61K 39/215; A61K 2039/53; C07K 14/005; C12N 7/00
See application file for complete search history.

(56) References Cited

U.S. PATENT DOCUMENTS

| | | |
|---|---|---|
| 2006/0035378 A1 | 2/2006 | Kochanek |
| 2006/0257852 A1 | 11/2006 | Rappuoli |
| 2007/0258999 A1* | 11/2007 | Plummer ............ C07K 14/005 424/221.1 |
| 2008/0044426 A1 | 2/2008 | De Jong |
| 2013/0216566 A1 | 8/2013 | Anderson |

FOREIGN PATENT DOCUMENTS

WO   2015153425 A1   10/2015

OTHER PUBLICATIONS

Wang et al.; Immunogenicity and antigenic relationships among spike proteins of porcine epidemic diarrhea virus subtypes G1 and G2; Archives of Virology; vol. 161, pp. 537-547, published online Nov. 15, 2015 (Year: 2015).*
Suo S, Ren Y, Li G, et al. Immune responses induced by DNA vaccines bearing Spike gene of PEDV combined with porcine IL-18. Virus Res. 2012;167(2):259-266.
Oh J, Lee KW, Choi HW, Lee C. Immunogenicity and protective efficacy of recombinant S1 domain of the porcine epidemic diarrhea virus spike protein. Arch Virol. 2014;159(11)12977-2987.
Meng F, Ren Y, Suo S, et al. Evaluation on the efficacy and immunogenicity of recombinant DNA plasmids expressing spike genes from porcine transmissible gastroenteritis virus and porcine epidemic diarrhea virus. PLoS One. 2013;8(3):e57468.
Kweon CH, Kwon BJ, Lee JG, Kwon GO, Kang YB. Derivation of attenuated porcine epidemic diarrhea virus (PEDV) as vaccine candidate [published correction appears in Vaccine Aug. 20, 1999;18(1-2):201], Vaccine. 1999;17(20-21):2546-2553.
Liu DQ, Ge JW, Qiao XY, Jiang YP, Liu SM, Li YJ. High-level mucosal and systemic immune responses induced by oral administration with Lactobacillus-expressed porcine epidemic diarrhea virus (PEDV) S1 region combined with Lactobacillus-expressed N protein. Appl Microbiol Biotechnol. 2012;93(6):2437-2446.
Bae JL, Lee JG, Kang TJ, Jang HS, Jang YS, Yang MS Induction of antigen-specific systemic and mucosal immune Yesponses by feeding animals transgenic plants expressing the antigen. Vaccine. 2003;21(25-26):4052-4058.
Kocherhans R, Bridgen A, Ackermann M, Tobler K Completion of the porcine epidemic diarrhoea coronavirus (PEDV) genome sequence. Virus Genes. 2001;23(2):137-144.

\* cited by examiner

*Primary Examiner* — Antonio Galisteo Gonzalez
(74) *Attorney, Agent, or Firm* — Riverside Law LLP

(57) ABSTRACT

Provided herein is a vaccine comprising a Porcine Epidemic Diarrhea Virus (PEDV) antigen. The antigen can be a consensus antigen. Also disclosed herein is a method of treating a porcine in need thereof, by administering the vaccine to the porcine.

20 Claims, 8 Drawing Sheets
Specification includes a Sequence Listing.

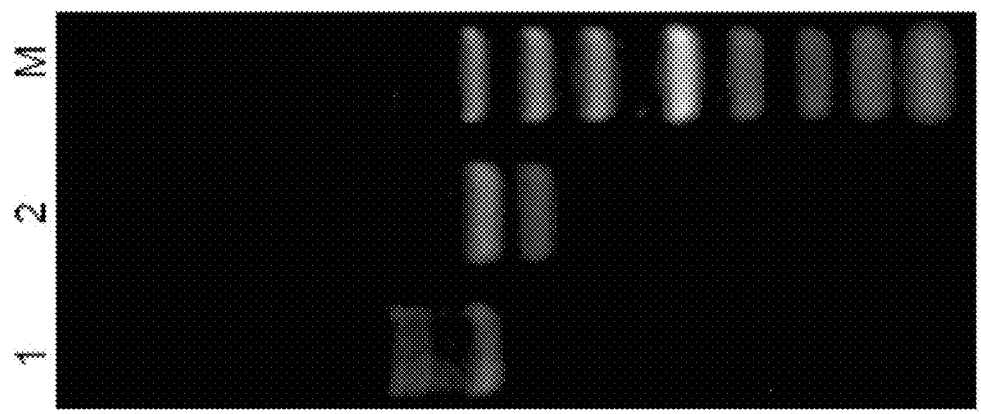
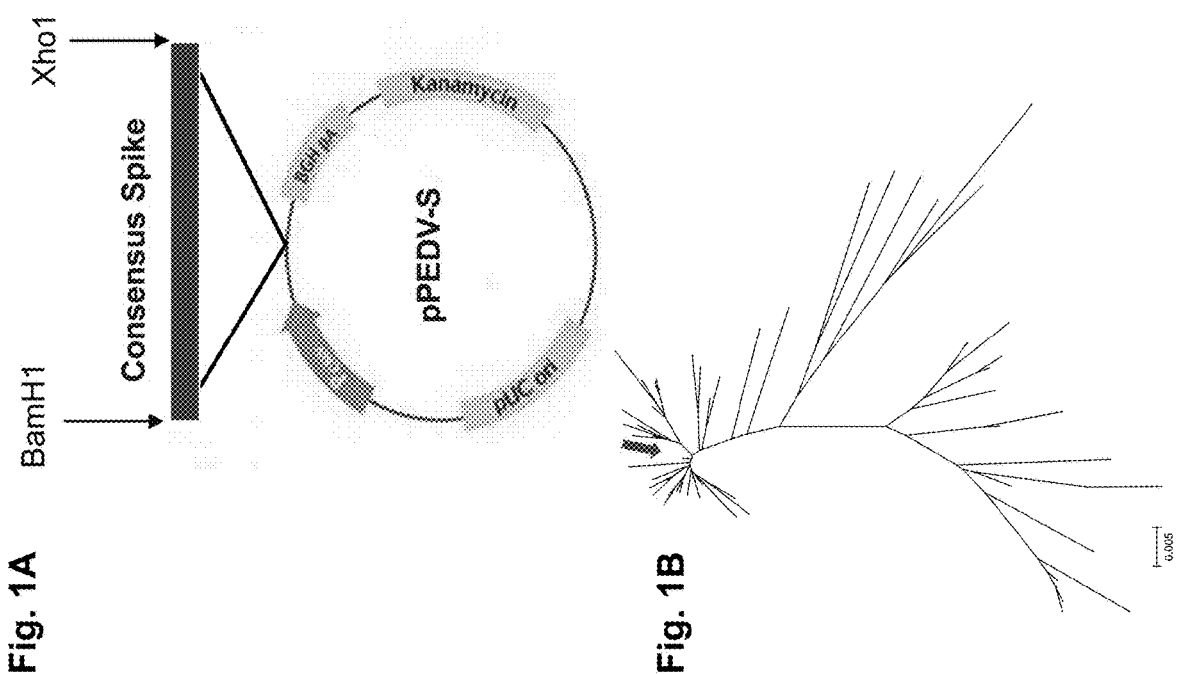

| SEQ ID NO | Description |
|---|---|
| 1 | PEDV-S optimized DNA consensus sequence from multi-alignment of 64 PEDV-S sequences |
| 2 | PEDV-S 64 optimized amino acid consensus sequence from multi-alignment of 64 PEDV-S sequences |
| 3 | Dominant T cell epitope, Peptide 65 |
| 4 | PEDV-S optimized DNA consensus sequence from multi-alignment of 64plus PEDV-S sequences |
| 5 | PEDV-S optimized amino acid consensus sequence from multi-alignment of 64plus PEDV-S sequences |
| 6 | Native leader DNA sequence |
| 7 | Native leader amino acid sequence |
| 8 | IgE leader DNA sequence |
| 9 | IgE leader amino acid sequence |

Figure 8

IMMUNOGENICITY OF AN OPTIMIZED SYNTHETIC CONSENSUS DNA VACCINE FOR PORCINE EPIDEMIC DIARRHEA VIRUS

CROSS-REFERENCE TO RELATED APPLICATIONS

This application is the U.S. national stage application filed under 35 U.S.C. § 371 claiming benefit to International Patent Application No. PCT/US16/14553, filed Jan. 22, 2016, which claims priority to U.S. Provisional Application No. 62/107,165, filed Jan. 23, 2015, which are hereby incorporated by reference in their entirety.

TECHNICAL FIELD

The present invention relates to a vaccine Porcine Epidemic Diarrhea Virus (PEDV) and a method of administering the vaccine.

BACKGROUND OF THE INVENTION

Porcine epidemic diarrhea virus (PEDV), an Alphacorona virus, is highly infectious, causing acute diarrhea and dehydration in pigs. While adult pigs usually recover from infection, mortality rates in suckling piglets can reach 100%.

PEDV has become of significant concern in several Asian countries and was first identified in the United States in 2013. Severe economic losses due to the more than 9000 confirmed cases in 33 states through January 2015 in the United States alone demonstrate the need for a safe and efficacious vaccine.

The commercially available traditional inactivated vaccines have many deficiencies, and evidence currently suggests that live PEDV vaccines can evolve into infectious. Also, there is now evidence that whole organism vaccines may stimulate cross-reactive immune responses to host proteins.

Thus, there is a need in the art for the development of effective vaccines against PEDV. The present invention satisfies this unmet need.

SUMMARY OF THE INVENTION

Aspects of the present invention include an immunogenic composition comprising a nucleic acid molecule, wherein the nucleic acid molecule comprises a nucleic acid sequence having at least about 90% identity over an entire length of the nucleic acid sequence selected from the group comprising SEQ ID NO:1 and SEQ ID NO:4.

In one aspect, the nucleic acid molecule comprises the nucleic acid sequence selected from the group comprising SEQ ID NO:1 and SEQ ID NO:4.

In one aspect, the nucleic acid sequence is linked to nucleotides encoding a leader sequence.

In one aspect, the leader sequence is encoded by the nucleic acid sequence of SEQ ID NO:6.

In one aspect, the leader sequence is an IgE leader sequence encoded by the nucleic acid sequence of SEQ ID NO:8.

In one aspect, the immunogenic composition of claim further comprises a peptide comprising an amino acid sequence having at least about 90% identity over an entire length of the amino acid sequence selected from the group comprising SEQ ID NO:2 and SEQ ID NO:5.

In one aspect, the peptide comprises an amino acid sequence having the amino acid sequence selected from the group comprising SEQ ID NO:2 and SEQ ID NO:5.

In one aspect, the amino acid sequence is linked to a leader sequence.

In one aspect, the leader sequence is comprises the amino acid sequence of SEQ ID NO:7.

In one aspect, the leader sequence is an IgE leader and comprises the amino acid sequence of SEQ ID NO:9.

In one aspect, the nucleic acid molecule comprises an expression vector.

In one aspect, the nucleic acid molecule is incorporated into a viral particle.

In one aspect, the immunogenic composition further comprises a pharmaceutically acceptable excipient.

In one aspect, the immunogenic composition further comprises an adjuvant.

An aspect of the invention includes an immunogenic composition comprising a nucleic acid molecule, wherein the nucleic acid molecule encodes a peptide comprising an amino acid sequence having at least about 90% identity over an entire length of the amino acid sequence selected from the group comprising SEQ ID NO:2 and SEQ ID NO:5.

In one aspect, the nucleic acid molecule encodes the peptide comprising the amino acid sequence selected from the group comprising SEQ ID NO:2 and SEQ ID NO:5.

In one aspect, the nucleic acid sequence is linked to nucleotides encoding a leader sequence.

In one aspect, the leader sequence is encoded by the nucleic acid sequence of SEQ ID NO:6.

In one aspect, the leader sequence is an IgE leader sequence encoded by the nucleic acid sequence of SEQ ID NO:8.

An aspect of the invention includes an immunogenic composition comprising peptide comprising an amino acid sequence having at least about 90% identity over an entire length of the amino acid sequence selected from the group comprising SEQ ID NO:2 and SEQ ID NO:5. In one aspect, the peptide comprises the amino acid sequence selected from the group comprising SEQ ID NO:2 and SEQ ID NO:5. In one aspect, the amino acid sequence is linked to a leader sequence. In one aspect, the leader sequence comprises the amino acid sequence of SEQ ID NO:7. In one aspect, the leader sequence is an IgE leader sequence. In one aspect an IgE leader sequence comprises the amino acid sequence of SEQ ID NO:9.

An aspect of the invention includes a nucleic acid molecule comprising a nucleic acid sequence having at least about 90% identity over an entire length of the nucleic acid sequence selected from the group comprising SEQ ID NO:1 and SEQ ID NO:4. In one aspect the nucleic acid sequence is selected from the group comprising SEQ ID NO:1 and SEQ ID NO:4. In one aspect, the nucleic acid sequence is linked to a leader sequence. In one aspect, the leader sequence comprises the nucleic acid sequence of SEQ ID NO:6. In one aspect, the leader sequence is an IgE leader sequence. In one aspect an IgE leader sequence comprises the nucleic acid sequence of SEQ ID NO:8.

An aspect of the invention includes a peptide comprising an amino acid sequence having at least about 90% identity over an entire length of the amino acid sequence selected from the group comprising SEQ ID NO:2 and SEQ ID NO:5. In one aspect, the comprises the amino acid sequence selected from the group comprising SEQ ID NO:2 and SEQ ID NO:5. In one aspect, the amino acid sequence is linked to a leader sequence. In one aspect, the leader sequence comprises the amino acid sequence of SEQ ID NO:7. In one aspect, the leader sequence is an IgE leader sequence. In one aspect an IgE leader sequence comprises the amino acid sequence of SEQ ID NO:9.

An aspect of the invention includes a method of inducing an immune response against a Porcine Epidemic Diarrhea Virus (PEDV) in a porcine in need thereof, the method comprising administering an immunogenic composition of the invention to the porcine. In one aspect, the administration includes at least one of electroporation and injection.

An aspect of the invention includes a method of protecting a porcine in need thereof from infection with a Porcine Epidemic Diarrhea Virus (PEDV), the method comprising administering an immunogenic composition of the invention to the porcine. In one aspect, the administration includes at least one of electroporation and injection.

An aspect of the invention includes a method of treating a porcine in need thereof against Porcine Epidemic Diarrhea Virus (PEDV), the method comprising administering an immunogenic composition of the invention to the porcine, wherein the porcine is thereby resistant to one or more Porcine Epidemic Diarrhea Virus (PEDV) strains. In one aspect, the administration includes at least one of electroporation and injection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1C, depict the schematic representation of the pPEDV-S DNA vaccine construct (FIG. 1A) and the gel electrophoresis of the digested and undigested construct (FIG. 1C). FIG. 1B depicts the diversity of all available full length sequences of PEDV S protein used for generating the consensus sequence, which is marked with an arrow.

FIG. 3 depicts the total antibody responses specific for each peptide pool Error bars are SEM.

FIG. 8 is a table depicting descriptions of the sequences associated with each SEQ ID NO referred to herein.

DETAILED DESCRIPTION

Figure 2:
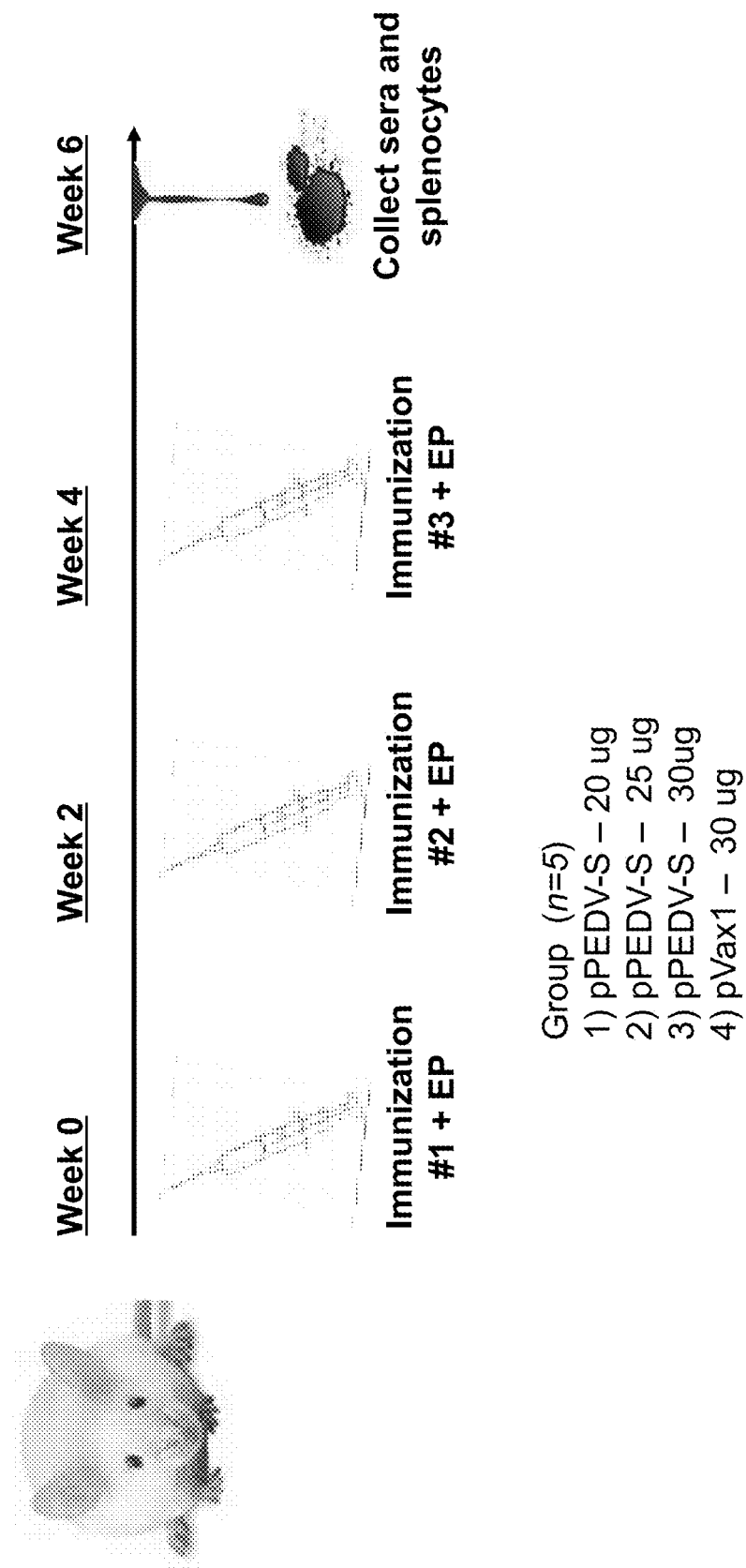
FIG. 2 is a schematic illustrating the immunization schedule for mice immunized with various doses of pPEDV-S or pVax1 (control).

Aspects of the present invention include a vaccine comprising a Porcine Epidemic Diarrhea Virus (PEDV) antigen. Further aspects of the present invention are treatments and/or preventions for this pathogenic virus using the disclosed vaccine.

The PEDV antigen of the invention can be a PEDV consensus spike antigen. The PEDV consensus spike antigen can be derived from the sequences of spike antigens from strains of PEVD, and thus, the PEVD consensus spike antigen of the invention is unique. The vaccine of the present invention can be widely applicable to multiple strains of PEDV because of the unique sequences of the PEDV consensus spike antigen. These unique sequences allow the vaccine to be universally protective against multiple strains of PEDV, including genetically diverse variants of PEDV.

The vaccine can be used to protect against and treat any number of strains of PEDV. The vaccine can elicit both humoral and cellular immune responses that target the PEDV spike antigen. The vaccine can elicit neutralizing antibodies and immunoglobulin G (IgG) antibodies that are reactive with the PEDV spike antigen. The vaccine can also elicit $CD8^+$ and $CD4^+$ T cell responses that are reactive to the PEDV spike antigen and produce interferon-gamma (IFN-γ), tumor necrosis factor alpha (TNF-α), and interleukin-2 (IL-2).

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccine described herein to enhance the immunogenicity of the antigen.

"Antibody" as used herein means an antibody of classes IgG, IgM, IgA, IgD or IgE, or fragments, fragments or derivatives thereof, including Fab, F(ab')$_2$, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to generate consensus sequences (or consensus antigens).

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein means a nucleic acid sequence or a portion thereof that encodes a polypeptide capable of eliciting an immune response in a mammal. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length wild type strain PEDV antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a PEDV protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that wants to or is in need of being immunized with the herein described vaccine.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

DESCRIPTION

The invention provides consensus sequence of a PEDV antigen. The PEDV consensus antigen can be a PEDV consensus spike antigen, a fragment thereof, a variant thereof, or a combination thereof. The PEDV spike antigen is capable of eliciting an immune response in a mammal against one or more PEDV strains. The PEDV spike antigen can comprise an epitope(s) that makes it particularly effective as an immunogen against which an anti-PEDV immune response can be induced.

The PEDV consensus spike antigen can be a consensus sequence derived from two or more strains of PEDV. The PEDV spike antigen can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the PEDV consensus spike antigen.

The PEDV consensus spike antigen can comprise a signal peptide such as an immunoglobulin signal peptide, for example, but not limited to, an immunoglobulin E (IgE) or immunoglobulin (IgG) signal peptide. In some embodiments, the PEDV consensus spike antigen can comprise a hemagglutinin (HA) tag. The PEDV consensus spike antigen can be designed to elicit stronger and broader cellular and/or humoral immune responses than a corresponding codon optimized spike antigen.

In some embodiments the PEDV consensus spike antigen is linked to a native leader sequence. In some embodiments, the PEDV consensus spike antigen is linked to an IgE leader sequence. In some embodiments the native leader has the amino acid sequence of SEQ ID NO: 7. In some embodiments the IgE leader has the sequence of SEQ ID NO: 9.

In one embodiment, the PEDV consensus spike antigen is encoded by the nucleic acid sequence of SEQ ID NO:1. In one embodiment, the PEDV consensus spike antigen is encoded by a nucleic acid molecule comprising the nucleic acid sequence of SEQ ID NO: 1 and the nucleic acid sequence of SEQ ID NO: 6 operably linked at the 5' end of SEQ ID NO:1. In one embodiment, the PEDV consensus spike antigen is encoded by a nucleic acid molecule comprising SEQ ID NO: 1 and the nucleic acid sequence of SEQ ID NO: 8 operably linked at the 5' end of SEQ ID NO:1 In one embodiment, the PEDV consensus spike antigen is encoded by the nucleic acid sequence of SEQ ID NO:4. In one embodiment, the PEDV consensus spike antigen is encoded by a nucleic acid molecule comprising the nucleic acid sequence of SEQ ID NO: 4 and the nucleic acid sequence of SEQ ID NO: 6 operably linked at the 5' end of SEQ ID NO:4. In one embodiment, the PEDV consensus spike antigen is encoded by a nucleic acid molecule comprising SEQ ID NO: 4 and the nucleic acid sequence of SEQ ID NO: 8 operably linked at the 5' end of SEQ ID NO: 4.

The PEDV consensus spike antigen can be encoded by the nucleic acid sequence of SEQ ID NO:1. In some embodiments, the PEDV consensus spike antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:1. In other embodiments, the PEDV consensus spike antigen can be encoded by the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2. In some embodiments the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:1 is operably linked to a nucleic acid sequence encoding a leader sequence, such as a native leader sequence or the IgE leader sequence. In some embodiments the leader sequence is encoded by SEQ ID NO:6. In some embodiments the leader sequence is encoded by SEQ ID NO:8. In some embodiments the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:1 is free of a nucleic acid molecule encoding a leader sequence.

The PEDV consensus spike antigen can be encoded by the nucleic acid sequence of SEQ ID NO:4. In some embodiments, the PEDV consensus spike antigen can be encoded by the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:4. In other embodiments, the PEDV consensus spike antigen can be encoded by the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:5. In some embodiments the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:4 is operably linked to nucleic acid sequence encoding a leader sequence, such as a native leader sequence or the IgE leader sequence. In some embodiments the leader sequence is encoded by SEQ ID NO:6. In some embodiments the leader sequence is encoded by SEQ ID NO:8. In some embodiments the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:4 is free of a nucleic acid sequence encoding a leader sequence.

In one embodiment, the PEDV consensus spike antigen comprises the amino acid sequence of SEQ ID NO:2. In some embodiments, the PEDV consensus spike antigen comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

In one embodiment, the PEDV consensus spike antigen comprises the amino acid sequence of SEQ ID NO:5. In some embodiments, the PEDV consensus spike antigen comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:5.

Immunogenic fragments of SEQ ID NO:2 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of SEQ ID NO:2. In some embodiments, the PEDV consensus spike antigen or immunogenic fragments are operably linked to a leader sequence, such as a native leader sequence or the IgE leader sequence. In some embodiments the leader sequence is SEQ ID NO:7. In some embodiments the leader sequence is SEQ ID NO:9. In some embodiments, immunogenic fragments are free of a leader sequence.

Immunogenic fragments of SEQ ID NO:5 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of SEQ ID NO:5. In some embodiments, the PEDV consensus spike antigen or immunogenic fragments are operably linked to a leader sequence, such as a native leader sequence or the IgE leader sequence. In some embodiments the leader sequence is SEQ ID NO:7. In some embodiments the leader sequence is SEQ ID NO:9. In some embodiments, immunogenic fragments are free of a leader sequence.

Immunogenic fragments of proteins with amino acid sequences homologous to immunogenic fragments of SEQ ID NO:2 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments are operably linked to a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:5 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:5. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments are operably linked to a leader sequence, such as for example an immunoglobulin leader, such as the IgE leader. In some embodiments, immunogenic fragments are free of a leader sequence.

Some embodiments relate to immunogenic fragments of SEQ ID NO:1. Immunogenic fragments can be at least 60%, at least 65%, at least 70%, at least 75%, at least 80%, at least 85%, at least 90%, at least 95%, at least 96%, at least 97%, at least 98% or at least 99% of SEQ ID NO:1. Immunogenic fragments can be at least 95%, at least 96%, at least 97% at least 98% or at least 99% homologous to fragments of SEQ ID NO:1. In some embodiments, immunogenic fragments are operably linked to sequences that encode a leader sequence, such as for example an immunoglobulin leader, such as the IgE leader. In some embodiments, immunogenic fragments are operably linked to SEQ ID NO:6. In some embodiments, immunogenic fragments are operably linked to SEQ ID NO:8. In some embodiments, fragments are free of coding sequences that encode a leader sequence.

Some embodiments relate to immunogenic fragments of SEQ ID NO:4. Immunogenic fragments can be at least 60%, at least 65%, at least 70%, at least 75%, at least 80%, at least 85%, at least 90%, at least 95%, at least 96%, at least 97%, at least 98% or at least 99% of SEQ ID NO:4. Immunogenic fragments can be at least 95%, at least 96%, at least 97% at least 98% or at least 99% homologous to fragments of SEQ ID NO:4. In some embodiments, immunogenic fragments are operably linked to sequences that encode a leader sequence, such as for example an immunoglobulin leader, such as the IgE leader. In some embodiments, immunogenic fragments are operably linked to SEQ ID NO:6. In some embodiments, immunogenic fragments are operably linked to SEQ ID NO:8. In some embodiments, fragments are free of coding sequences that encode a leader sequence.

Vaccine

Provided herein are immunogenic compositions, such as vaccines, comprising a Porcine Epidemic Diarrhea Virus (PEDV) antigen, a fragment thereof, a variant thereof, or a combination thereof. The vaccine can be used to protect against any number of strains of PEDV, thereby treating, preventing, and/or protecting against PEDV based pathologies. The vaccine can significantly induce an immune response of a subject (e.g., porcine) administered with the vaccine, thereby protecting against and treating PEDV infection.

The vaccine can be a DNA vaccine, a peptide vaccine, or a combination DNA and peptide vaccine. The DNA vaccine can include a nucleic acid sequence encoding the PEDV consensus spike antigen. The nucleic acid sequence can be DNA, RNA, cDNA, a variant thereof, a fragment thereof, or a combination thereof. The nucleic acid sequence can also include additional sequences that encode linker, leader, or tag sequences that are linked to the PEDV consensus spike antigen by a peptide bond. The peptide vaccine can include a PEDV consensus antigenic peptide, a PEDV consensus spike antigen, a variant thereof, a fragment thereof, or a combination thereof. The combination DNA and peptide vaccine can include the above described nucleic acid sequence encoding the PEDV consensus spike antigen.

The vaccine can induce a humoral immune response in the subject administered the vaccine. The induced humoral immune response can be specific for the PEDV consensus spike antigen. The induced humoral immune response can be reactive with the PEDV consensus spike antigen. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the vaccine can include an increased level of neutralizing antibodies associated with the subject administered the vaccine as compared to a subject not administered the vaccine. The neutralizing antibodies can be specific for the PEDV consensus spike antigen. The neutralizing antibodies can be reactive with the PEDV consensus spike antigen. The neutralizing antibodies can provide protection against and/or treatment of PEDV infection and its associated pathologies in the subject administered the vaccine.

The humoral immune response induced by the vaccine can include an increased level of IgG antibodies associated with the subject administered the vaccine as compared to a subject not administered the vaccine. These IgG antibodies can be specific for the PEDV consensus spike antigen. These IgG antibodies can be reactive with the PEDV consensus spike antigen. Preferably, the humoral response is cross-reactive against two or more strains of PEDV. The level of IgG antibody associated with the subject administered the vaccine can be increased by about 1.5-fold to about 16-fold, about 2-fold to about 12-fold, or about 3-fold to about 10-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the vaccine.

The vaccine can induce a cellular immune response in the subject administered the vaccine. The induced cellular immune response can be specific for the PEDV consensus spike antigen. The induced cellular immune response can be reactive to the PEDV consensus spike antigen. Preferably, the cellular response is cross-reactive against two or more strains of PEDV. The induced cellular immune response can include eliciting a CD8$^+$ T cell response. The elicited CD8$^+$ T cell response can be reactive with the PEDV antigen. The elicited CD8$^+$ T cell response can be polyfunctional. The induced cellular immune response can include eliciting a CD8$^+$ T cell response, in which the CD8$^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8$^+$ T cell response associated with the subject administered the vaccine as compared to the subject not administered the vaccine. The CD8$^+$ T cell response associated with the subject administered the vaccine can be increased by about 2-fold to about 30-fold, about 3-fold to about 25-fold, or about 4-fold to about 20-fold as compared to the subject not administered the vaccine. The CD8$^+$ T cell response associated with the subject administered the vaccine can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the vaccine.

The induced cellular immune response can include an increased frequency of CD3$^+$CD8$^+$ T cells that produce IFN-$\gamma$. The frequency of CD3$^+$CD8$^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3$^+$CD8$^+$ T cells that produce TNF-$\alpha$. The frequency of CD3$^+$CD8$^+$ TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to the subject not administered the vaccine.

The induced cellular immune response can include an increased frequency of CD3$^+$CD8$^+$ T cells that produce IL-2. The frequency of CD3$^+$CD8$^-$IL-2$^+$ T cells associated with the subject administered the vaccine can be increased by at least about 0.5-fold, 1.0-fold, 1.5-fold, 2.0-fold, 2.5-fold, 3.0-fold, 3.5-fold, 4.0-fold, 4.5-fold, or 5.0-fold as compared to the subject not administered the vaccine.

The induced cellular immune response can include an increased frequency of CD3$^+$CD8$^+$ T cells that produce both IFN-$\gamma$ and TNF-$\alpha$. The frequency of CD3$^+$CD8$^+$IFN-$\gamma^+$TNF-$\alpha^+$ T cells associated with the subject administered the vaccine can be increased by at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, or 180-fold as compared to the subject not administered the vaccine.

The cellular immune response induced by the vaccine can include eliciting a CD4$^+$ T cell response. The elicited CD4$^+$ T cell response can be reactive with the PEDV antigen. The elicited CD4$^+$ T cell response can be polyfunctional. The induced cellular immune response can include eliciting a CD4$^+$ T cell response, in which the CD4$^+$ T cells produce IFN-$\gamma$, TNF-$\alpha$, IL-2, or a combination of IFN-$\gamma$ and TNF-$\alpha$.

The induced cellular immune response can include an increased frequency of CD3$^+$CD4$^+$ T cells that produce IFN-$\gamma$. The frequency of CD3$^+$CD4$^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3$^+$CD4$^+$ T cells that produce TNF-$\alpha$. The frequency of CD3$^+$CD4$^+$ TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to the subject not administered the vaccine.

The induced cellular immune response can include an increased frequency of CD3$^+$CD4$^+$ T cells that produce IL-2. The frequency of CD3$^+$CD4$^+$IL-2$^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 45-fold, 50-fold, 55-fold, or 60-fold as compared to the subject not administered the vaccine.

The induced cellular immune response can include an increased frequency of CD3$^+$CD4$^+$ T cells that produce both IFN-$\gamma$ and TNF-$\alpha$. The frequency of CD3$^+$CD4$^+$IFN-$\gamma^+$TNF-$\alpha^+$ associated with the subject administered the vaccine can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to the subject not administered the vaccine.

The vaccine of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The vaccine can further induce an immune response when administered to different tissues such as the muscle or skin. The vaccine can further induce an immune response when administered via electroporation, or injection, or subcutaneously, or intramuscularly.

Vector

The vaccine can comprise one or more vectors that include a nucleic acid encoding the PEDV consensus spike antigen. The one or more vectors can be capable of expressing the PEDV consensus spike antigen. The vector can have a nucleic acid sequence containing an origin of replication. The vector can be a plasmid, bacteriophage, bacterial artificial chromosome or yeast artificial chromosome. The vector can be either a self-replicating extrachromosomal vector or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

In some embodiments, the vector further comprises a nucleic acid sequence encoding a leader sequence, such as a native leader sequence or an IgE leader sequence, attached to an N-terminal end of the coding sequence and operably linked to the promoter. In some embodiments, the native leader has the amino acid sequence set forth in SEQ ID NO:7. In some embodiments, the IgE leader has the amino acid sequence set forth in SEQ ID NO:9. The vector can further include a polyadenylation sequence attached to the C-terminal end of the coding sequence.

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Excipients and Other Components of the Vaccine

The vaccine of the invention may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml.

The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in an alternative plasmid or are delivered as proteins in combination with the plasmid above in the vaccine.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Method of Vaccination

Also provided herein is a method of treating, protecting against, and/or preventing disease in a subject in need thereof by administering the vaccine to the subject. Administration of the vaccine to the subject can induce or elicit an immune response in the subject. The induced immune response can be used to treat, prevent, and/or protect against disease, for example, pathologies relating to PEDV infection. The induced immune response provided the subject administered the vaccine resistance to one or more PEDV strains.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced humoral immune response can include IgG antibodies and/or neutralizing antibodies that are reactive to the antigen. The induced cellular immune response can include a $CD8^+$ T cell response, which is induced by about 2-fold to about 30-fold, about 3-fold to about 25-fold, or about 4-fold to about 20-fold.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a porcine.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the subject, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Feigner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

Kit

Provided herein is a kit, which can be used for treating a subject using the method of vaccination described above. The kit can comprise the vaccine.

The kit can also comprise instructions for carrying out the vaccination method described above and/or how to use the kit. Instructions included in the kit can be affixed to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

The present invention has multiple aspects, illustrated by the following non-limiting examples.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Consensus PEDV-Spike Vaccine

The spike (S) protein is the surface glycoprotein PEDV, which can induce neutralizing antibodies and is considered to be a primary target antigen for developing an effective vaccine against PEDV. The Spike protein consists of the S1 and S2 domains and is responsible for viral attachment and fusion with the host cell membrane.

Described herein is the development of a novel consensus DNA vaccine encoding the Spike protein only, where the nucleic acid sequence encoding the Spike protein was inserted into a eukaryotic DNA expression vector. By designing a DNA based vaccine expressing a consensus S immunogen, the vaccine may protect against various circulating strains of PEDV while taking advantage of the safety and ease of production advantages of DNA vaccines. The data presented herein demonstrates that, in comparison with the control pVax immunized group, pPEDV-S significantly increased the number of IFNγ producing cells and induced total IgG endpoint titers of $10^4$ specific for the PEDV spike protein. Dominant T cell epitopes and dominant linear antibody binding domains within the PEDV S protein were identified by epitope mapping with 15mer peptides overlapping by 11 amino acids. This investigation is a first step in the development of novel consensus DNA based vaccines against PEDV.

The consensus amino acid sequence was generated by creating a consensus of 64 different amino acid sequences of PEDV-S protein. The diversity of all available full length sequences are shown in FIG. 1B. The consensus is marked with the arrow. The amino acid sequence of a consensus PEDV-spike of the vaccine is set forth in SEQ ID NO: 2.

The nucleic acid sequence encoding SEQ ID NO: 2, an amino acid sequence of the consensus PEDV-spike of the vaccine, is set forth in SEQ ID NO: 1.

FIG. 1A depicts the schematic representation off the pPEDV-S DNA vaccine construct, comprising a nucleic acid sequence encoding the consensus spike protein. The gel electrophoresis of the digested and undigested construct is shown in FIG. 1C.

Experiments were conducted using mice which were immunized with various doses of pPEDV-S or pVax1, the empty vector control, with electroporation (EP) 3 times every 2 weeks (FIG. 2). Sera and splenocytes from individual mice (n=5) were isolated 2 weeks after the third immunization. ELISA and ELISpot assays were performed to measure the humoral and cellular immune responses.

Figure 3:
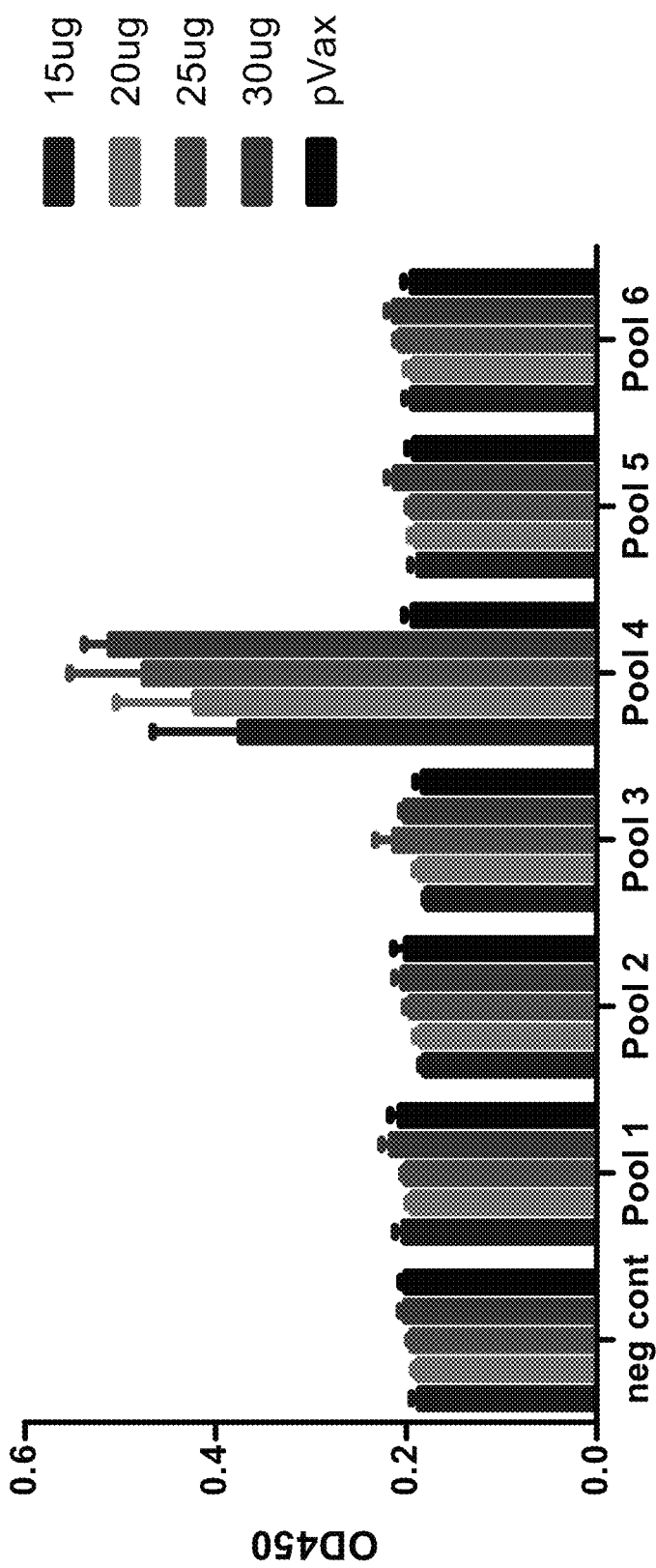
FIG. 3 depicts the results of experiments demonstrating that immunization with pPEDV-S induced a robust antibody response specific for PEDV Spike protein. Sera was isolated from immunized mice and binding IgG antibody response for specific linear epitopes of the consensus PEDV-spike sequence was evaluated by peptide ELISA.

15mer peptides overlapping by 11 amino acids spanning the entire consensus PEDV-Spike sequence were mixed into 6 pools. Sera was isolated from immunized mice and binding IgG levels specific for linear epitopes were evaluated by peptide ELISA. Total antibody responses specific for each peptide pool was observed and is shown in FIG. 3. The IgG antibody response induced by pPEDV-S was reactive only to pool 4. Further characterization of the dominant antibody binding epitopes is in progress.

Figure 4:
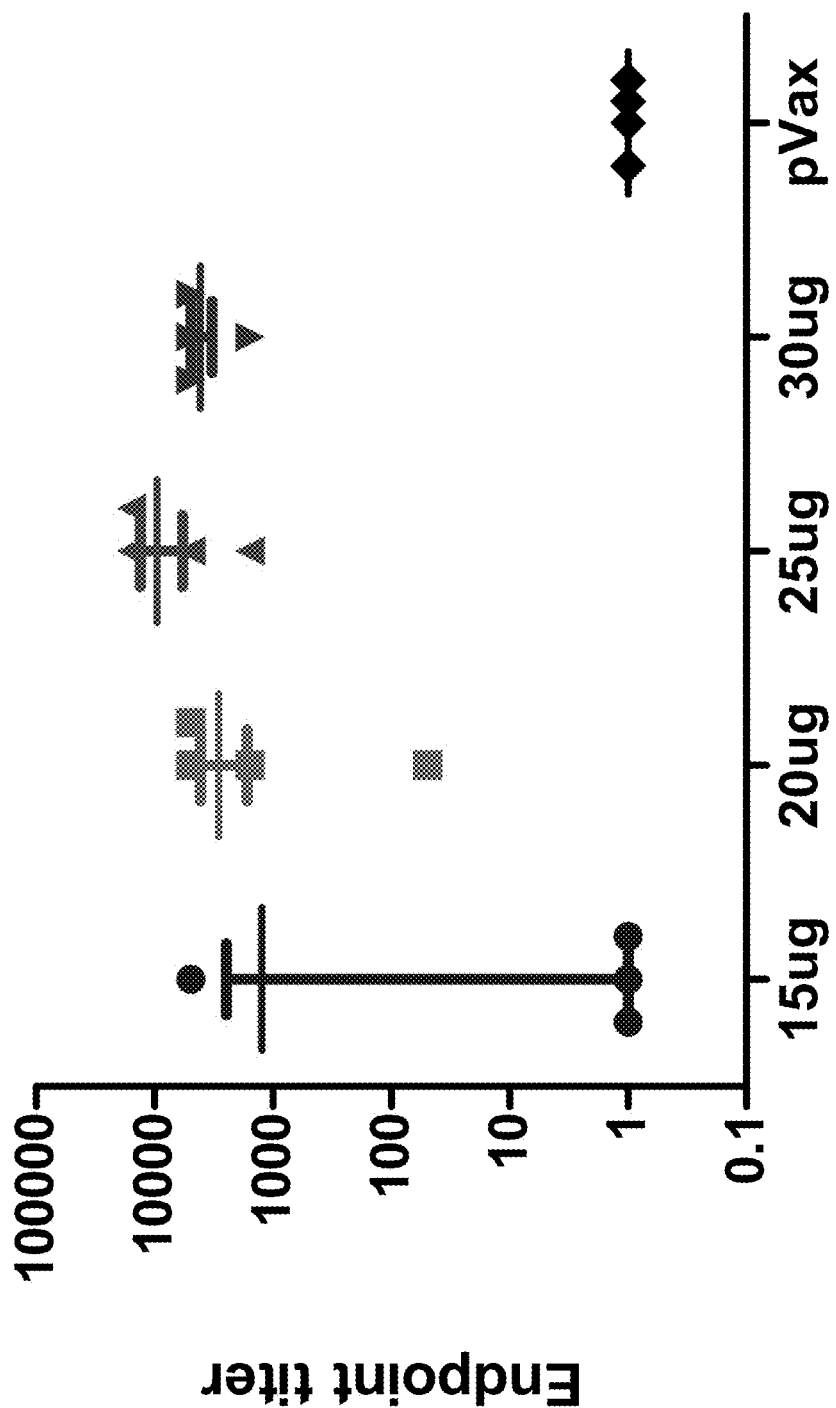
FIG. 4 is a graph depicting the endpoint tiers calculated for antibody binding to pool 4. Average data from 5 mice in each immunization group are shown. Error bars are SEM.

Endpoint titers were calculated for antibody binding to Pool 4. Total IgG endpoint titers to pool 4 show that pPEDV-S induced high levels of PEDV spike protein specific antibodies (FIG. 4). All immunized animals seroconverted.

Figure 5:
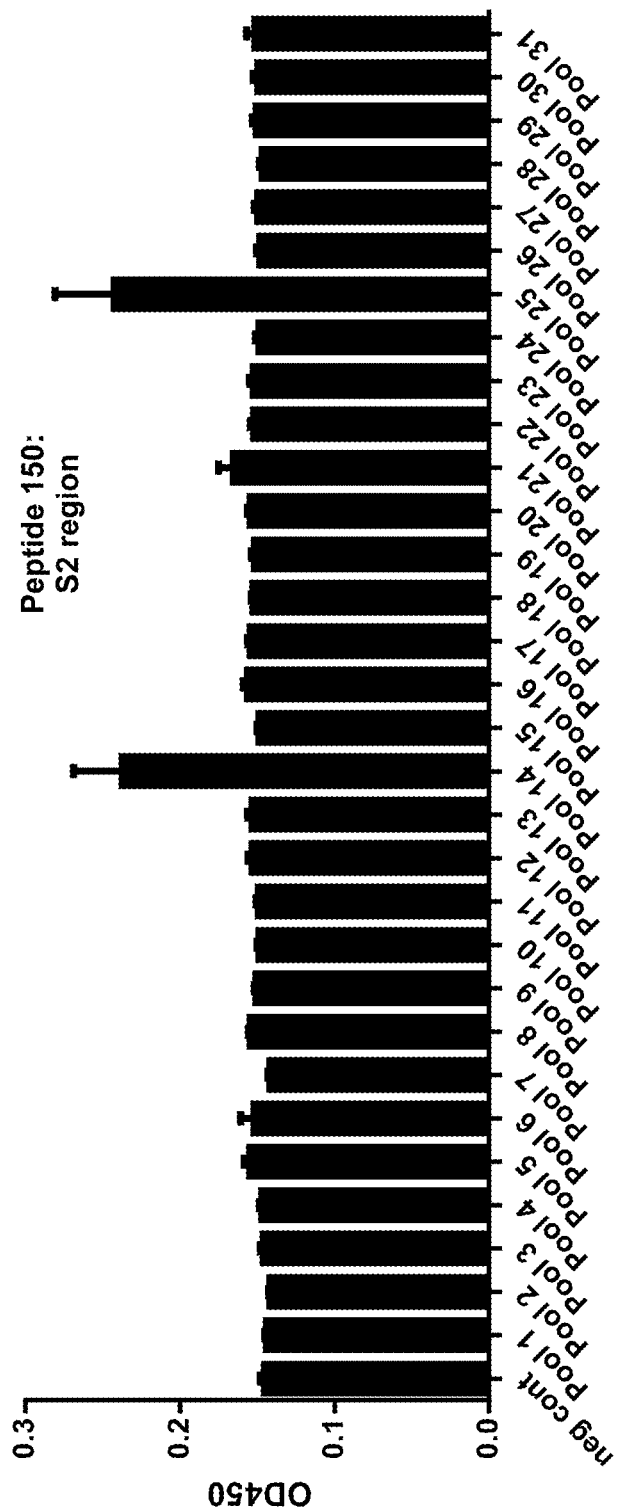
FIG. 5 is a graph depicting the results of experiments for determining dominant linear binding antibody epitopes. Sera was isolated from immunized mice and binding IgG levels specific for linear epitopes were evaluated by peptide ELISA. Average data from 5 mice immunized with 25 µg pPEDV-S are shown. Error bars are SEM.

Sera was isolated from immunized mice and binding IgG levels specific for linear epitopes were evaluated by peptide ELISA. Average data from 5 mice immunized with 25 ug pPEDV-S are shown in FIG. 5. Dominant epitope region were identified in the S2 region of the Spike protein.

Figure 6:
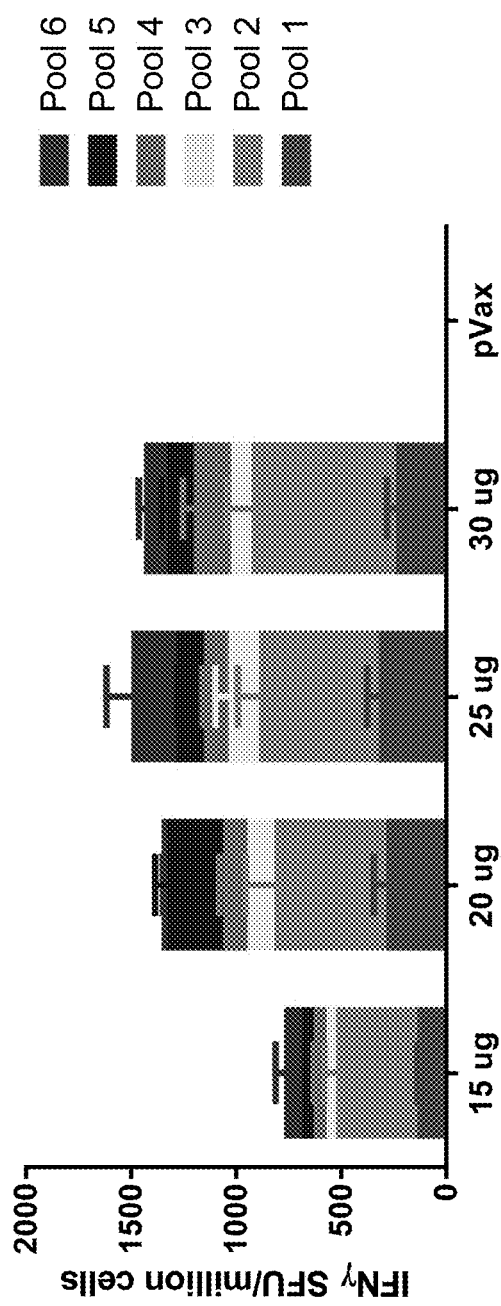
FIG. 6 is a graph depicting the results of experiments demonstrating that immunization with pPEDV-S induced a robust IFNγ T cell response specific for PEDV spike protein. Splenocytes were isolated from immunized mice and T cell responses were evaluated by ELISpot assay. Average data from 5 mice in each immunization group are shown. Error bars are SEM.
Figure 7:
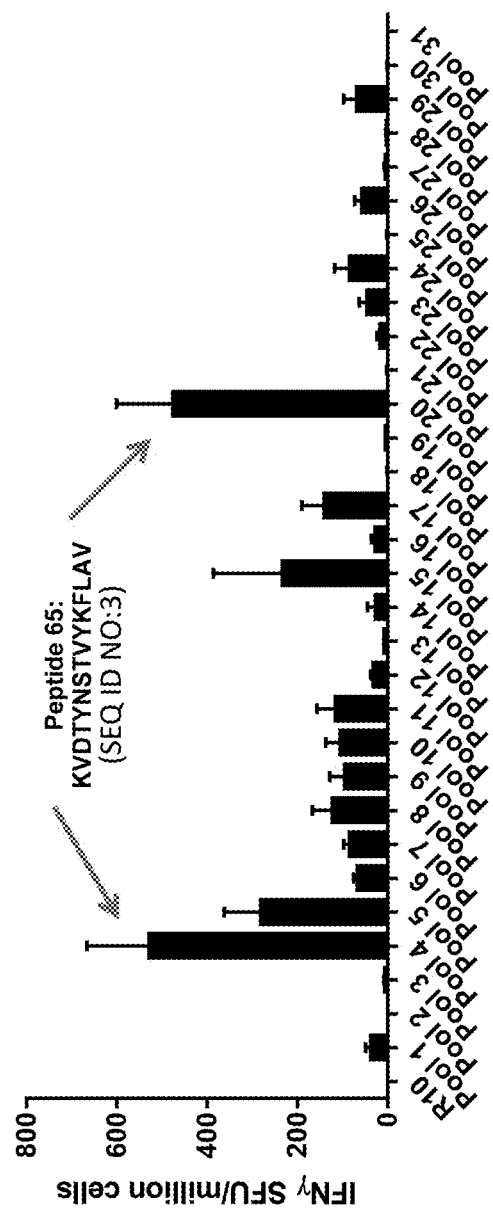
FIG. 7 is a graph depicting the results of experiments which identified dominant T cell epitopes. Splenocytes were isolated from immunized mice and T cell responses were evaluated by ELISpot assay. Average data from 5 mice immunized with 30 ug pPEDV-S are shown. Error bars are SEM.

IFNγ ELISpot assay was conducted which demonstrated a robust T cell response in pPEDV-S vaccinated animals (FIG. 6 and FIG. 7). Splenocytes were isolated from immunized mice and T cell responses were evaluated by ELISpot assay (FIG. 6 and FIG. 7). The T cell response was reactive all the peptide pools, though the majority of the response was to pool 4 and pool 20. Dominant T cell epitope was identified as peptide 65 (KVDTYNSTVYKFLAV (SEQ ID NO: 3)) (FIG. 7).

Example 2: Alternative Consensus PEDV-S Sequences of the Invention

An additional consensus PEDV-S amino acid sequence was generated by creating a consensus of more than 64 different amino acid sequences of PEDV-S protein. The consensus amino acid sequence is set forth in SEQ ID NO: 5. The nucleic acid sequence encoding SEQ ID NO: 5 is set forth in SEQ ID NO:4.

SEQ ID NOs: 2, and 5 may be additionally linked to a leader sequence at its N-terminal end. Leader sequences may be native, such as the amino acid sequence as set forth in SEQ ID NO:7 and encoded by the nucleic acid sequence set forth in SEQ ID NO: 6, or may be a IgE leader sequence such as the amino acid sequence set forth in SEQ ID NO: 9 and encoded by the nucleic acid sequence set forth in SEQ ID NO: 8. A description of all sequence IDs is provided in FIG. 8.

In summary, described herein is the development and testing of a synthetic DNA consensus PEDV-Spike vaccine. It was demonstrated that pPEDV-S was immunogenic in mice. Seroconversion and IFN-g producing T cells were observed in all immunized animals. The dominant T cell epitope as well as dominant antibody binding domains were identified. It is believed that his is the first consensus synthetic DNA based vaccine targeting PEDV to elicit both humoral and cellular responses. The use of a synthetic consensus sequence in this non live platform may improve the vaccine's efficacy across various circulating PEDV strains.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunogenic composition comprising a nucleic acid molecule, wherein the nucleic acid molecule comprises a nucleic acid sequence selected from the group consisting of SEQ ID NO:1 and SEQ ID NO:4.

2. The immunogenic composition of claim 1, wherein the nucleic acid sequence is linked to nucleotides that encode a leader sequence.

3. The immunogenic composition of claim 2, wherein the leader sequence is encoded by a nucleic acid sequence selected from the group consisting of SEQ ID NO:6 and SEQ ID NO: 8.

4. The immunogenic composition of claim 1, further comprising a peptide comprising an amino acid sequence having an amino acid sequence selected from the group consisting of SEQ ID NO:2 and SEQ ID NO:5.

5. The immunogenic composition of claim 4, wherein the amino acid sequence is linked to a leader sequence.

6. The immunogenic composition of claim 5, wherein the leader sequence comprises an amino acid sequence selected from the group consisting of SEQ ID NO:7 and SEQ ID NO:9.

7. The immunogenic composition of claim 1, wherein the nucleic acid molecule comprises an expression vector.

8. The immunogenic composition of claim 1, wherein the nucleic acid molecule is incorporated into a viral particle.

9. The immunogenic composition of claim 1, further comprising a pharmaceutically acceptable excipient.

10. The immunogenic composition of claim 1, further comprising an adjuvant.

11. A nucleic acid molecule comprising a nucleic acid sequence having at least about 90% identity over the entire length of a nucleic acid sequence selected from the group consisting of SEQ ID NO:1 and SEQ ID NO:4.

12. The nucleic acid molecule of claim 11, comprising a nucleic acid sequence selected from the group consisting of SEQ ID NO:1 and SEQ ID NO:4.

13. The nucleic acid molecule of claim 11, wherein the nucleic acid molecule is linked to nucleotides encoding a leader sequence.

14. The nucleic acid molecule of claim 13, wherein the leader sequence is encoded by a nucleic acid sequence selected from the group consisting of SEQ ID NO:6 and SEQ ID NO: 8.

15. A method of inducing an immune response against a Porcine Epidemic Diarrhea Virus (PEDV) in a porcine in need thereof, the method comprising administering the immunogenic composition of claim 1 to the porcine.

16. The method of claim 15, wherein administering includes at least one of electroporation and injection.

17. A method of protecting a porcine in need thereof from infection with a Porcine Epidemic Diarrhea Virus (PEDV), the method comprising administering the immunogenic composition of claim 1 to the porcine.

18. The method of the claim 17, wherein administering includes at least one of electroporation and injection.

19. A method of treating a porcine in need thereof against Porcine Epidemic Diarrhea Virus (PEDV), the method comprising administering the immunogenic composition of claim 1 to the porcine, wherein the porcine is thereby resistant to one or more Porcine Epidemic Diarrhea Virus (PEDV) strains.

20. The method of claim 19, wherein administering includes at least one of electroporation and injection.

* * * * *

SEQUENCE LISTING

```
<160> NUMBER OF SEQ ID NOS: 9

<210> SEQ ID NO 1
<211> LENGTH: 4119
<212> TYPE: DNA
<213> ORGANISM: Artificial Sequence
<220> FEATURE:
<223> OTHER INFORMATION: PEDV-S 64 consensus

<400> SEQUENCE: 1
ctgcctcagg atgtcacaag atgctctgct aataccaact tcaggagatt ctttagcaag      60
tttaatgtgc aggcaccagc tgtggtcgtg ctcggcggat acctgcctat cggggagaat     120
cagggcggcg tgaactccac ttggtattgc gctggccagc accctaccgc atctggagtg     180
catgggatct tcctgtcaca cattcgggga gggcatgggt tcgagatcgg cattagccag     240
gagccatttg acccttccgg gtaccagctg tatctccaca aggccaccaa cggcaataca     300
aacgcaactg cccgactgag gatctgccag ttccctagca ttaagaccct ggggcccaca     360
gccaacaatg acgtgaccac aggccgcaat tgtctgttta acaaagctat tcccgcacac     420
atgtccgatg gcgagcattc tgtcgtggga atcacttggg acaacgatag ggtcaccgtg     480
ttctccgaca agatctacta tttctacttt aaaaacgatt ggagcagagt ggccaccaag     540
tgctataatt ccggcggatg tgctatgcag tacgtctatg agcccacata ctatatgctg     600
aacgtgactt ctgccggcga agacggaatt tcataccagc catgcaccgc caattgtatc     660
ggctatgccg ctaacgtgtt cgctacagag cccaatggcc acatcccaga aggattcagc     720
tttaacaatt ggtttctgct ctctaacgat tcaaccctgg tgcatggcaa ggtcgtgtcc     780
aatcagcccc tgctcgtgaa ctgcctgctc gccatcccaa aaatctacgg actggggcag     840
ttctttagct tcaaccagac catcgacgga gtctgtaatg gagcagcagt gcagcgagca     900
```

```
ccagaggctc tgaggttcaa tatcaacgat acaagtgtca ttctggctga aggaagcatc    960
gtgctccaca ctgcactggg gaccaacctc tcattcgtgt gcagtaatag ctccgaccct   1020
catctggcaa catttgccat cccactcggc gccactcagg tcccttacta ttgtttcctg   1080
aaggtggata catacaactc cactgtctat aaatttctgg ccgtgctgcc cccaaccgtc   1140
agggagatcg tgattacaaa gtacggcgac gtgtacgtga acggcttcgg atacctgcac   1200
ctcggactgc tcgatgccgt gaccatcaac ttcaccgggc atggcactga cgatgacgtg   1260
tccggcttct ggaccattgc atctacaaac tttgtcgacg ccctgatcga ggtgcaggga   1320
accgccatcc agagaattct gtactgcgat gaccctgtct cacagctcaa atgtagtcag   1380
gtggctttcg acctggatga cggcttttat cccatttctt cacggaacct gctcagtcac   1440
gagcagccca tcagcttcgt gaccctgcca agcttcaatg atcactcctt tgtcaacatc   1500
acagtgtcag ccagttttgg gggccattca ggagccaacc tgattgctag tgacactacc   1560
atcaatgggt tcagtagctt ttgcgtggat actagacagt tcaccatcag tctgttttac   1620
aatgtcacca actcatacgg ctatgtgagc aagtcccagg acagcaactg tcccttcaca   1680
ctgcagtccg tcaacgatta cctctctttc tcaaagttct gcgtgagtac cagcctgctc   1740
gcttctgcat gtacaatcga cctgttcggg tacccagagt ttggctcctc ttcaggaggg   1800
ggcgtgaagt tcacttccct gtatttccag tttaccaagg gagagctgat caccgggaca   1860
cctaaacccc tcgaaggggt caccgacgtg agcttcatga cactggacgt gtgcaccaag   1920
tacacaatct acggcttcaa aggagagggg atcattactc tgaccaacag tagctttctc   1980
gccggcgtgt actatacctc cgactctgga cagctgctcg ccttcaagaa tgtgacttct   2040
ggcgctgtct actcagtgac cccatgtagc ttcagcgagc aggctgcata tgtggatgac   2100
gatatcgtcg gagtgatttc ctctctgtca agtagcacat tcaacagcac tagggagctg   2160
ccagggttct tttaccacag caatgacggc tccaactgca ccgaacctgt cctggtgtac   2220
tccaacattg gcgtctgtaa gagcgggtcc atcggctatg tgccttctca gtcaggacag   2280
gtcaaaatcg cccctacagt gactgggaat atcagcattc ccacaaactt cagtatgagc   2340
attagaactg agtacctgca gctctataac accccgtct ctgtggactg cgccacatac   2400
gtgtgcaatg gcaacagccg atgcaagcag ctgctcactc agtataccgc cgcttgtaaa   2460
accatcgaaa gtgctctgca gctcagcgca aggctggagt ccgtcgaagt gaactctatg   2520
ctgacaattt cagaggaagc actgcagctc gccactatct cctctttcaa tggcgacgga   2580
tacaacttca ccaacgtgct gggcgtctcc gtgtatgatc ccgcctctgg aagagtcgtg   2640
cagaagcggt ccttcatcga ggacctgctg ttcaacaagg tcgtgaccaa cgggctgggc   2700
acagtggacg aagattacaa gaggtgctct aacggccgat cagtcgcaga cctggtgtgc   2760
gctcagtact atagcggggt catggtgctg ccaggagtcg tggatgcaga gaaactgcac   2820
atgtactccg cctctctgat cggagggatg gtgctcggcg gattaccgc agccgctctg   2880
cctttttcct acgctgtgca ggcaagactg aactatctgg ccctccagac agacgtgctg   2940
cagcggaatc agcagctgct cgccgagagt ttcaatagcg ccatcggaaa cattaccagt   3000
gcttttgaga gcgtgaagga agcaatctcc cagacttcta aagggctgaa caccgtcgcc   3060
cacgctctca caaaggtgca ggaagtcgtg aatagccagg gagcagccct gacacagctc   3120
actgtgcagc tgcagcacaa cttccaggcc atctcaagta gcatcgacga tatctacagc   3180
aggctggaca ttctcagtgc tgacgtgcag gtggataggc tgatcaccgg cagactgtcc   3240
```

```
gccctcaacg ctttcgtcgc acagaccctg acaaagtaca cagaggtgca ggcatctcgc    3300
aagctggccc agcagaaagt caacgaatgc gtgaaatcac agagtcagcg atacggattc    3360 tgtggggcg acggggagca catctttcc ctggtgcagg ctgcacctca gggactgctc      3420
```

-continued

Gly Ile Ser Tyr Gln Pro Cys Thr Ala Asn Cys Ile Gly Tyr Ala Ala
    210                 215                 220

Asn Val Phe Ala Thr Glu Pro Asn Gly His Ile Pro Glu Gly Phe Ser
225                 230                 235                 240

Phe Asn Asn Trp Phe Leu Leu Ser Asn Asp Ser Thr Leu Val His Gly
                245                 250                 255

Lys Val Val Ser Asn Gln Pro Leu Leu Val Asn Cys Leu Leu Ala Ile
            260                 265                 270

Pro Lys Ile Tyr Gly Leu Gly Gln Phe Ser Phe Asn Gln Thr Ile
        275                 280                 285

Asp Gly Val Cys Asn Gly Ala Ala Val Gln Arg Ala Pro Glu Ala Leu
    290                 295                 300

Arg Phe Asn Ile Asn Asp Thr Ser Val Ile Leu Ala Glu Gly Ser Ile
305                 310                 315                 320

Val Leu His Thr Ala Leu Gly Thr Asn Leu Ser Phe Val Cys Ser Asn
                325                 330                 335

Ser Ser Asp Pro His Leu Ala Thr Phe Ala Ile Pro Leu Gly Ala Thr
            340                 345                 350

Gln Val Pro Tyr Tyr Cys Phe Leu Lys Val Asp Thr Tyr Asn Ser Thr
        355                 360                 365

Val Tyr Lys Phe Leu Ala Val Leu Pro Pro Thr Val Arg Glu Ile Val
370                 375                 380

Ile Thr Lys Tyr Gly Asp Val Tyr Val Asn Gly Phe Gly Tyr Leu His
385                 390                 395                 400

Leu Gly Leu Leu Asp Ala Val Thr Ile Asn Phe Thr Gly His Gly Thr
                405                 410                 415

Asp Asp Asp Val Ser Gly Phe Trp Thr Ile Ala Ser Thr Asn Phe Val
            420                 425                 430

Asp Ala Leu Ile Glu Val Gln Gly Thr Ala Ile Gln Arg Ile Leu Tyr
        435                 440                 445

Cys Asp Asp Pro Val Ser Gln Leu Lys Cys Ser Gln Val Ala Phe Asp
    450                 455                 460

Leu Asp Asp Gly Phe Tyr Pro Ile Ser Ser Arg Asn Leu Leu Ser His
465                 470                 475                 480

Glu Gln Pro Ile Ser Phe Val Thr Leu Pro Ser Phe Asn Asp His Ser
                485                 490                 495

Phe Val Asn Ile Thr Val Ser Ala Ser Phe Gly Gly His Ser Gly Ala
            500                 505                 510

Asn Leu Ile Ala Ser Asp Thr Thr Ile Asn Gly Phe Ser Ser Phe Cys
        515                 520                 525

Val Asp Thr Arg Gln Phe Thr Ile Ser Leu Phe Tyr Asn Val Thr Asn
    530                 535                 540

Ser Tyr Gly Tyr Val Ser Lys Ser Gln Asp Ser Asn Cys Pro Phe Thr
545                 550                 555                 560

Leu Gln Ser Val Asn Asp Tyr Leu Ser Phe Ser Lys Phe Cys Val Ser
                565                 570                 575

Thr Ser Leu Leu Ala Ser Ala Cys Thr Ile Asp Leu Phe Gly Tyr Pro
            580                 585                 590

Glu Phe Gly Ser Ser Gly Gly Val Lys Phe Thr Ser Leu Tyr
        595                 600                 605

Phe Gln Phe Thr Lys Gly Glu Leu Ile Thr Gly Thr Pro Lys Pro Leu
    610                 615                 620

Glu Gly Val Thr Asp Val Ser Phe Met Thr Leu Asp Val Cys Thr Lys

```
                625               630               635               640
           Tyr Thr Ile Tyr Gly Phe Lys Gly Glu Gly Ile Ile Thr Leu Thr Asn
                       645               650               655

Ser Ser Phe Leu Ala Gly Val Tyr Tyr Thr Ser Asp Ser Gly Gln Leu
                       660               665               670

Leu Ala Phe Lys Asn Val Thr Ser Gly Ala Val Tyr Ser Val Thr Pro
                       675               680               685

Cys Ser Phe Ser Glu Gln Ala Ala Tyr Val Asp Asp Ile Val Gly
                       690               695               700

Val Ile Ser Ser Leu Ser Ser Ser Thr Phe Asn Ser Thr Arg Glu Leu
           705               710               715               720

Pro Gly Phe Phe Tyr His Ser Asn Asp Gly Ser Asn Cys Thr Glu Pro
                               725               730               735

Val Leu Val Tyr Ser Asn Ile Gly Val Cys Lys Ser Gly Ser Ile Gly
                           740               745               750

Tyr Val Pro Ser Gln Ser Gly Gln Val Lys Ile Ala Pro Thr Val Thr
                           755               760               765

Gly Asn Ile Ser Ile Pro Thr Asn Phe Ser Met Ser Ile Arg Thr Glu
           770               775               780

Tyr Leu Gln Leu Tyr Asn Thr Pro Val Ser Val Asp Cys Ala Thr Tyr
           785               790               795               800

Val Cys Asn Gly Asn Ser Arg Cys Lys Gln Leu Leu Thr Gln Tyr Thr
                           805               810               815

Ala Ala Cys Lys Thr Ile Glu Ser Ala Leu Gln Leu Ser Ala Arg Leu
                           820               825               830

Glu Ser Val Glu Val Asn Ser Met Leu Thr Ile Ser Glu Glu Ala Leu
                           835               840               845

Gln Leu Ala Thr Ile Ser Ser Phe Asn Gly Asp Gly Tyr Asn Phe Thr
                           850               855               860

Asn Val Leu Gly Val Ser Val Tyr Asp Pro Ala Ser Gly Arg Val Val
           865               870               875               880

Gln Lys Arg Ser Phe Ile Glu Asp Leu Leu Phe Asn Lys Val Val Thr
                           885               890               895

Asn Gly Leu Gly Thr Val Asp Glu Asp Tyr Lys Arg Cys Ser Asn Gly
                           900               905               910

Arg Ser Val Ala Asp Leu Val Cys Ala Gln Tyr Tyr Ser Gly Val Met
                           915               920               925

Val Leu Pro Gly Val Val Asp Ala Glu Lys Leu His Met Tyr Ser Ala
                           930               935               940

Ser Leu Ile Gly Gly Met Val Leu Gly Gly Phe Thr Ala Ala Ala Leu
           945               950               955               960

Pro Phe Ser Tyr Ala Val Gln Ala Arg Leu Asn Tyr Leu Ala Leu Gln
                           965               970               975

Thr Asp Val Leu Gln Arg Asn Gln Gln Leu Leu Ala Glu Ser Phe Asn
                           980               985               990

Ser Ala Ile Gly Asn Ile Thr Ser Ala Phe Glu Ser Val Lys Glu Ala
                           995               1000              1005

Ile Ser Gln Thr Ser Lys Gly Leu Asn Thr Val Ala His Ala Leu
                   1010              1015              1020

Thr Lys Val Gln Glu Val Val Asn Ser Gln Gly Ala Ala Leu Thr
                   1025              1030              1035

Gln Leu Thr Val Gln Leu Gln His Asn Phe Gln Ala Ile Ser Ser
                   1040              1045              1050
```

```
Ser Ile Asp Asp Ile Tyr Ser Arg Leu Asp Ile Leu Ser Ala Asp
    1055                1060                1065

Val Gln Val Asp Arg Leu Ile Thr Gly Arg Leu Ser Ala Leu Asn
    1070                1075                1080

Ala Phe Val Ala Gln Thr Leu Thr Lys Tyr Thr Glu Val Gln Ala
    1085                1090                1095

Ser Arg Lys Leu Ala Gln Gln Lys Val Asn Glu Cys Val Lys Ser
    1100                1105                1110

Gln Ser Gln Arg Tyr Gly Phe Cys Gly Gly Asp Gly Glu His Ile
    1115                1120                1125

Phe Ser Leu Val Gln Ala Ala Pro Gln Gly Leu Leu Phe Leu His
    1130                1135                1140

Thr Val Leu Val Pro Gly Asp Phe Val Asp Val Ile Ala Ile Ala
    1145                1150                1155

Gly Leu Cys Val Asn Asp Glu Ile Ala Leu Thr Leu Arg Glu Pro
    1160                1165                1170

Gly Leu Val Leu Phe Thr His Glu Leu Gln Asn His Thr Ala Thr
    1175                1180                1185

Glu Tyr Phe Val Ser Ser Arg Arg Met Phe Glu Pro Arg Lys Pro
    1190                1195                1200

Thr Val Ser Asp Phe Val Gln Ile Glu Ser Cys Val Val Thr Tyr
    1205                1210                1215

Val Asn Leu Thr Arg Asp Gln Leu Pro Asp Val Ile Pro Asp Tyr
    1220                1225                1230

Ile Asp Val Asn Lys Thr Leu Asp Glu Ile Leu Ala Ser Leu Pro
    1235                1240                1245

Asn Arg Thr Gly Pro Ser Leu Pro Leu Asp Val Phe Asn Ala Thr
    1250                1255                1260

Tyr Leu Asn Leu Thr Gly Glu Ile Ala Asp Leu Glu Gln Arg Ser
    1265                1270                1275

Glu Ser Leu Arg Asn Thr Thr Glu Glu Leu Gln Ser Leu Ile Tyr
    1280                1285                1290

Asn Ile Asn Asn Thr Leu Val Asp Leu Glu Trp Leu Asn Arg Val
    1295                1300                1305

Glu Thr Tyr Ile Lys Trp Pro Trp Trp Val Trp Leu Ile Ile Phe
    1310                1315                1320

Ile Val Leu Ile Phe Val Val Ser Leu Leu Val Phe Cys Cys Ile
    1325                1330                1335

Ser Thr Gly Cys Cys Gly Cys Cys Gly Cys Cys Gly Ala Cys Phe
    1340                1345                1350

Ser Gly Cys Cys Arg Gly Pro Arg Leu Gln Pro Tyr Glu Phe Glu
    1355                1360                1365

Lys Val His Val Gln
    1370

<210> SEQ ID NO 3
<211> LENGTH: 15
<212> TYPE: PRT
<213> ORGANISM: Artificial Sequence
<220> FEATURE:
<223> OTHER INFORMATION: Dominant T cell epitope

<400> SEQUENCE: 3

Lys Val Asp Thr Tyr Asn Ser Thr Val Tyr Lys Phe Leu Ala Val
1               5                   10                  15
```

<210> SEQ ID NO 4
<211> LENGTH: 4110
<212> TYPE: DNA
<213> ORGANISM: Artificial Sequence
<220> FEATURE:
<223> OTHER INFORMATION: PEDV-S 64plus consensus

<400> SEQUENCE: 4
ctgcctcagg atgtcacaag atgctctgct aataccaact tcaggagatt ctttagcaag 60
tttaatgtgc aggcaccagc tgtggtcgtg ctcggcggat acctgcctat cggggagaat 120
cagggcgtga actccacttg gtattgcgct ggccagcacc ctaccgcatc tggagtgcat 180
gggatcttcc tgtcacacat tcggggaggg catgggttcg agatcggcat tagccaggag 240
ccatttgacc cttccgggta ccagctgtat ctccacaagg ccaccaacgg caatacaaac 300
gcaactgccc gactgaggat ctgccagttc cctagcatta agaccctggg gcccacagcc 360
aacaatgacg tgaccacagg ccgcaattgt ctgtttaaca aagctattcc cgcacacatg 420
tccgatggcg agcattctgt cgtgggaatc acttgggaca acgatagggt caccgtgttc 480
tccgacaaga tctactattt ctactttaaa aacgattgga gcagagtggc caccaagtgc 540
tataattccg gcggatgtgc tatgcagtac gtctatgagc ccacatacta tatgctgaac 600
gtgacttctg ccggcgaaga cggaatttca taccagccat gcaccgccaa ttgtatcggc 660
tatgccgcta acgtgttcgc tacagagccc aatggccaca tcccagaagg attcagcttt 720
aacaattggt ttctgctctc taacgattca accctggtgc atggcaaggt cgtgtccaat 780
cagcccctgc tcgtgaactg cctgctcgcc atcccaaaaa tctacggact ggggcagttc 840
tttagcttca accagaccat cgacggagtc tgtaatggag cagcagtgca gcgagcacca 900
gaggctctga ggttcaatat caacgataca agtgtcattc tggctgaagg aagcatcgtg 960
ctccacactg cactggggac caacctctca ttcgtgtgca gtaatagctc cgaccctcat 1020
ctggcaacat ttgccatccc actcggcgcc actcaggtcc cttactattg tttcctgaag 1080
gtggatacat acaactccac tgtctataaa tttctggccg tgctgccccc aaccgtcagg 1140
gagatcgtga ttacaaagta cggcgacgtg tacgtgaacg gcttcggata cctgcacctc 1200
ggactgctcg atgccgtgac catcaacttc accgggcatg gcactgacga tgacgtgtcc 1260
ggcttctgga ccattgcatc tacaaacttt gtcgacgccc tgatcgaggt gcagggaacc 1320
gccatccaga gaattctgta ctgcgatgac cctgtctcac agctcaaatg tagtcaggtg 1380
gctttcgacc tggatgacgg cttttatccc atttcttcac ggaacctgct cagtcacgag 1440
cagcccatca gcttcgtgac cctgccaagc ttcaatgatc actcctttgt caacatcaca 1500
gtgtcagcca gttttggggg ccattcagga gccaacctga ttgctagtga cactaccatc 1560
aatgggttca gtagcttttg cgtggatact agacagttca ccatcagtct gttttacaat 1620
gtcaccaact catacggcta tgtgagcaag tcccaggaca gcaactgtcc cttcacactg 1680
cagtccgtca acgattacct ctctttctca aagttctgcg tgagtaccag cctgctcgct 1740
tctgcatgta caatcgacct gttcgggtac ccagagtttg gctccggcgt gaagttcact 1800
tccctgtatt tccagtttac caagggagag ctgatcaccg ggacacctaa acccctcgaa 1860
ggggtcaccg acgtgagctt catgacactg gacgtgtgca ccaagtacac aatctacggc 1920
ttcaaaggag aggggatcat tactctgacc aacagtagct ttctcgccgg cgtgtactat 1980
acctccgact ctggacagct gctcgccttc aagaatgtga cttctggcgc tgtctactca 2040

```
gtgaccccat gtagcttcag cgagcaggct gcatatgtgg atgacgatat cgtcggagtg    2100
atttcctctc tgtcaagtag cacattcaac agcactaggg agctgccagg gttctttttac   2160 cacagcaatg acggctccaa ctgcaccgaa cctgtcctgg tgtactccaa cattggcgtc    2220
tgtaagagcg gtccatcgg  ctatgtgcct tctcagtcag acaggtcaa  aatcgcccct    2280 acagtgactg ggaatatcag cattcccaca aacttcagta tgagcattag aactgagtac   2340
ctgcagctct ataacacccc cgtctctgtg gactgcgcca catacgtgtg caatggcaac    2400
agccgatgca agcagctgct cactcagtat accgccgctt gtaaaaccat cgaaagtgct    2460
ctgcagctca cgcaaggct  ggagtccgtc gaagtgaact ctatgctgac aatttcagag    2520
gaagcactgc agctcgccac tatctcctct ttcaatggcg acggatacaa cttcaccaac    2580
gtgctgggcg tctccgtgta tgatcccgcc tctggaagag tcgtgcagaa gcggtccttc    2640
atcgaggacc tgctgttcaa caaggtcgtg accaacgggc tgggcacagt ggacgaagat    2700
tacaagaggt gctctaacgg ccgatcagtc gcagacctgg tgtgcgctca gtactatagc    2760
ggggtcatgg tgctgccagg agtcgtggat gcagagaaac tgcacatgta ctccgcctct    2820
ctgatcggag ggatggtgct cggcggattc accgcagcag ccgctctgcc ttttttcctac   2880 gctgtgcagg caagactgaa ctatctggcc ctccagacag acgtgctgca gcggaatcag    2940
cagctgctcg ccgagagttt caatagcgcc atcggaaaca ttaccagtgc ttttgagagc    3000
gtgaaggaag caatctccca gacttctaaa gggctgaaca ccgtcgccca cgctctcaca   3060
aaggtgcagg aagtcgtgaa tagccaggga gcagccctga cacagctcac tgtgcagctg    3120
cagcacaact tccaggccat ctcaagtagc atcgacgata tctacagcag gctggacatt    3180
ctcagtgctg acgtgcaggt ggataggctg atcaccggca gactgtccgc cctcaacgct    3240
ttcgtcgcac agaccctgac aaagtacaca gaggtgcagg catctcgcaa gctggcccag    3300
cagaaagtca cgaatgcgt  gaaatcacag agtcagcgat acggattctg tgggggcgac    3360
ggggagcaca tcttttcccct ggtgcaggct gcacctcagg gactgctctt cctgcatacc    3420
gtcctcgtgc ccggcgactt tgtcgatgtg atcgcaattg ccggactgtg cgtgaacgat    3480
gagatcgccc tgaccctccg agaaccagga ctggtgctct tcacacacga gctgcagaat    3540
catactgcta ccgaatactt cgtgtcctct cggcgcatgt ttgagccccg gaagccaacc    3600
gtcagcgact tcgtgcagat cgaatcctgc gtcgtgactt acgtgaacct gacccgcgac    3660
cagctcccag atgtcatccc tgactatatt gatgtgaaca aaactctgga tgagatcctg    3720
gcctctctcc ccaatcgaac cggacctagc ctgccactcg acgtgttcaa tgcaacatac    3780
ctgaacctca ctggggaaat cgctgatctg gagcagcgga gcgaatccct ccgcaacaca    3840
actgaggaac tgcagtccct catctacaat attaacaata cactggtcga cctggagtgg    3900
ctgaaccgag tggaaactta tatcaagtgg ccatggtggg tctggctgat catttttcatc    3960 gtgctcattt ttgtcgtgtc cctgctcgtg ttctgctgta tttctaccgg atgctgtggg    4020
tgctgtggct gctgtggagc ctgcttttca ggatgttgtc gggggccaag actccagcca    4080
tacgaagcat ttgaaaaggt ccacgtccag                                     4110
```

<210> SEQ ID NO 5
<211> LENGTH: 1370
<212> TYPE: PRT
<213> ORGANISM: Artificial Sequence
<220> FEATURE:
<223> OTHER INFORMATION: PEDV-S 64plus consensus

<400> SEQUENCE: 5

```
Leu Pro Gln Asp Val Thr Arg Cys Ser Ala Asn Thr Asn Phe Arg Arg
1               5                   10                  15

Phe Phe Ser Lys Phe Asn Val Gln Ala Pro Ala Val Val Leu Gly
            20                  25                  30

Gly Tyr Leu Pro Ile Gly Glu Asn Gln Gly Val Asn Ser Thr Trp Tyr
            35                  40                  45

Cys Ala Gly Gln His Pro Thr Ala Ser Gly Val His Gly Ile Phe Leu
    50                  55                  60

Ser His Ile Arg Gly Gly His Gly Phe Glu Ile Gly Ile Ser Gln Glu
65                  70                  75                  80

Pro Phe Asp Pro Ser Gly Tyr Gln Leu Tyr Leu His Lys Ala Thr Asn
                85                  90                  95

Gly Asn Thr Asn Ala Thr Ala Arg Leu Arg Ile Cys Gln Phe Pro Ser
            100                 105                 110

Ile Lys Thr Leu Gly Pro Thr Ala Asn Asn Asp Val Thr Thr Gly Arg
            115                 120                 125

Asn Cys Leu Phe Asn Lys Ala Ile Pro Ala His Met Ser Asp Gly Glu
    130                 135                 140

His Ser Val Val Gly Ile Thr Trp Asp Asn Asp Arg Val Thr Val Phe
145                 150                 155                 160

Ser Asp Lys Ile Tyr Tyr Phe Tyr Phe Lys Asn Asp Trp Ser Arg Val
                165                 170                 175

Ala Thr Lys Cys Tyr Asn Ser Gly Gly Cys Ala Met Gln Tyr Val Tyr
            180                 185                 190

Glu Pro Thr Tyr Tyr Met Leu Asn Val Thr Ser Ala Gly Glu Asp Gly
            195                 200                 205

Ile Ser Tyr Gln Pro Cys Thr Ala Asn Cys Ile Gly Tyr Ala Ala Asn
210                 215                 220

Val Phe Ala Thr Glu Pro Asn Gly His Ile Pro Glu Gly Phe Ser Phe
225                 230                 235                 240

Asn Asn Trp Phe Leu Leu Ser Asn Asp Ser Thr Leu Val His Gly Lys
            245                 250                 255

Val Val Ser Asn Gln Pro Leu Leu Val Asn Cys Leu Leu Ala Ile Pro
            260                 265                 270

Lys Ile Tyr Gly Leu Gly Gln Phe Phe Ser Phe Asn Gln Thr Ile Asp
            275                 280                 285

Gly Val Cys Asn Gly Ala Ala Val Gln Arg Ala Pro Glu Ala Leu Arg
    290                 295                 300

Phe Asn Ile Asn Asp Thr Ser Val Ile Leu Ala Glu Gly Ser Ile Val
305                 310                 315                 320

Leu His Thr Ala Leu Gly Thr Asn Leu Ser Phe Val Cys Ser Asn Ser
            325                 330                 335

Ser Asp Pro His Leu Ala Thr Phe Ala Ile Pro Leu Gly Ala Thr Gln
            340                 345                 350

Val Pro Tyr Tyr Cys Phe Leu Lys Val Asp Thr Tyr Asn Ser Thr Val
            355                 360                 365

Tyr Lys Phe Leu Ala Val Leu Pro Pro Thr Val Arg Glu Ile Val Ile
    370                 375                 380

Thr Lys Tyr Gly Asp Val Tyr Val Asn Gly Phe Gly Tyr Leu His Leu
385                 390                 395                 400

Gly Leu Leu Asp Ala Val Thr Ile Asn Phe Thr Gly His Gly Thr Asp
                405                 410                 415
```

```
Asp Asp Val Ser Gly Phe Trp Thr Ile Ala Ser Thr Asn Phe Val Asp
                420                 425                 430

Ala Leu Ile Glu Val Gln Gly Thr Ala Ile Gln Arg Ile Leu Tyr Cys
            435                 440                 445

Asp Asp Pro Val Ser Gln Leu Lys Cys Ser Gln Val Ala Phe Asp Leu
        450                 455                 460

Asp Asp Gly Phe Tyr Pro Ile Ser Ser Arg Asn Leu Leu Ser His Glu
465                 470                 475                 480

Gln Pro Ile Ser Phe Val Thr Leu Pro Ser Phe Asn Asp His Ser Phe
                485                 490                 495

Val Asn Ile Thr Val Ser Ala Ser Phe Gly Gly His Ser Gly Ala Asn
            500                 505                 510

Leu Ile Ala Ser Asp Thr Thr Ile Asn Gly Phe Ser Ser Phe Cys Val
        515                 520                 525

Asp Thr Arg Gln Phe Thr Ile Ser Leu Phe Tyr Asn Val Thr Asn Ser
    530                 535                 540

Tyr Gly Tyr Val Ser Lys Ser Gln Asp Ser Asn Cys Pro Phe Thr Leu
545                 550                 555                 560

Gln Ser Val Asn Asp Tyr Leu Ser Phe Ser Lys Phe Cys Val Ser Thr
                565                 570                 575

Ser Leu Leu Ala Ser Ala Cys Thr Ile Asp Leu Phe Gly Tyr Pro Glu
            580                 585                 590

Phe Gly Ser Gly Val Lys Phe Thr Ser Leu Tyr Phe Gln Phe Thr Lys
        595                 600                 605

Gly Glu Leu Ile Thr Gly Thr Pro Lys Pro Leu Glu Gly Val Thr Asp
    610                 615                 620

Val Ser Phe Met Thr Leu Asp Val Cys Thr Lys Tyr Thr Ile Tyr Gly
625                 630                 635                 640

Phe Lys Gly Glu Gly Ile Ile Thr Leu Thr Asn Ser Ser Phe Leu Ala
                645                 650                 655

Gly Val Tyr Tyr Thr Ser Asp Ser Gly Gln Leu Leu Ala Phe Lys Asn
            660                 665                 670

Val Thr Ser Gly Ala Val Tyr Ser Val Thr Pro Cys Ser Phe Ser Glu
        675                 680                 685

Gln Ala Ala Tyr Val Asp Asp Ile Val Gly Val Ile Ser Ser Leu
    690                 695                 700

Ser Ser Ser Thr Phe Asn Ser Thr Arg Glu Leu Pro Gly Phe Phe Tyr
705                 710                 715                 720

His Ser Asn Asp Gly Ser Asn Cys Thr Glu Pro Val Leu Val Tyr Ser
                725                 730                 735

Asn Ile Gly Val Cys Lys Ser Gly Ser Ile Gly Tyr Val Pro Ser Gln
            740                 745                 750

Ser Gly Gln Val Lys Ile Ala Pro Thr Val Thr Gly Asn Ile Ser Ile
        755                 760                 765

Pro Thr Asn Phe Ser Met Ser Ile Arg Thr Glu Tyr Leu Gln Leu Tyr
    770                 775                 780

Asn Thr Pro Val Ser Val Asp Cys Ala Thr Tyr Val Cys Asn Gly Asn
785                 790                 795                 800

Ser Arg Cys Lys Gln Leu Leu Thr Gln Tyr Thr Ala Ala Cys Lys Thr
                805                 810                 815

Ile Glu Ser Ala Leu Gln Leu Ser Ala Arg Leu Glu Ser Val Glu Val
            820                 825                 830

Asn Ser Met Leu Thr Ile Ser Glu Glu Ala Leu Gln Leu Ala Thr Ile
```

-continued

|   | 835 |   |   | 840 |   |   | 845 |   |   |   |   |
|---|---|---|---|---|---|---|---|---|---|---|---|
| Ser | Ser | Phe | Asn | Gly | Asp | Gly | Tyr | Asn | Phe | Thr | Asn | Val | Leu | Gly | Val |

Ser Val Tyr Asp Pro Ala Ser Gly Arg Val Val Gln Lys Arg Ser Phe
865              870                875             880

Ile Glu Asp Leu Leu Phe Asn Lys Val Val Thr Asn Gly Leu Gly Thr
              885              890              895

Val Asp Glu Asp Tyr Lys Arg Cys Ser Asn Gly Arg Ser Val Ala Asp
900                  905                 910

Leu Val Cys Ala Gln Tyr Tyr Ser Gly Val Met Val Leu Pro Gly Val
       915               920              925

Val Asp Ala Glu Lys Leu His Met Tyr Ser Ala Ser Leu Ile Gly Gly
930                  935                 940

Met Val Leu Gly Gly Phe Thr Ala Ala Ala Leu Pro Phe Ser Tyr
945                  950               955             960

Ala Val Gln Ala Arg Leu Asn Tyr Leu Ala Leu Gln Thr Asp Val Leu
             965               970              975

Gln Arg Asn Gln Gln Leu Leu Ala Glu Ser Phe Asn Ser Ala Ile Gly
            980                985               990

Asn Ile Thr Ser Ala Phe Glu Ser Val Lys Glu Ala Ile Ser Gln Thr
            995              1000             1005

Ser Lys Gly Leu Asn Thr Val Ala His Ala Leu Thr Lys Val Gln
1010                 1015                1020

Glu Val Val Asn Ser Gln Gly Ala Ala Leu Thr Gln Leu Thr Val
1025                 1030                1035

Gln Leu Gln His Asn Phe Gln Ala Ile Ser Ser Ser Ile Asp Asp
1040                 1045                1050

Ile Tyr Ser Arg Leu Asp Ile Leu Ser Ala Asp Val Gln Val Asp
1055                 1060                1065

Arg Leu Ile Thr Gly Arg Leu Ser Ala Leu Asn Ala Phe Val Ala
1070                 1075                1080

Gln Thr Leu Thr Lys Tyr Thr Glu Val Gln Ala Ser Arg Lys Leu
1085                 1090                1095

Ala Gln Gln Lys Val Asn Glu Cys Val Lys Ser Gln Ser Gln Arg
1100                 1105                1110

Tyr Gly Phe Cys Gly Gly Asp Gly Glu His Ile Phe Ser Leu Val
1115                 1120                1125

Gln Ala Ala Pro Gln Gly Leu Leu Phe Leu His Thr Val Leu Val
1130                 1135                1140

Pro Gly Asp Phe Val Asp Val Ile Ala Ile Ala Gly Leu Cys Val
1145                 1150                1155

Asn Asp Glu Ile Ala Leu Thr Leu Arg Glu Pro Gly Leu Val Leu
1160                 1165                1170

Phe Thr His Glu Leu Gln Asn His Thr Ala Thr Glu Tyr Phe Val
1175                 1180                1185

Ser Ser Arg Arg Met Phe Glu Pro Arg Lys Pro Thr Val Ser Asp
1190                 1195                1200

Phe Val Gln Ile Glu Ser Cys Val Val Thr Tyr Val Asn Leu Thr
1205                 1210                1215

Arg Asp Gln Leu Pro Asp Val Ile Pro Asp Tyr Ile Asp Val Asn
1220                 1225                1230

Lys Thr Leu Asp Glu Ile Leu Ala Ser Leu Pro Asn Arg Thr Gly
1235                 1240                1245

```
Pro Ser Leu Pro Leu Asp Val Phe Asn Ala Thr Tyr Leu Asn Leu
    1250            1255                1260

Thr Gly Glu Ile Ala Asp Leu Glu Gln Arg Ser Glu Ser Leu Arg
    1265            1270                1275

Asn Thr Thr Glu Glu Leu Gln Ser Leu Ile Tyr Asn Ile Asn Asn
    1280            1285                1290

Thr Leu Val Asp Leu Glu Trp Leu Asn Arg Val Glu Thr Tyr Ile
    1295            1300                1305

Lys Trp Pro Trp Trp Val Trp Leu Ile Ile Phe Ile Val Leu Ile
    1310            1315                1320

Phe Val Val Ser Leu Leu Val Phe Cys Cys Ile Ser Thr Gly Cys
    1325            1330                1335

Cys Gly Cys Cys Gly Cys Cys Gly Ala Cys Phe Ser Gly Cys Cys
    1340            1345                1350

Arg Gly Pro Arg Leu Gln Pro Tyr Glu Ala Phe Glu Lys Val His
    1355            1360                1365

Val Gln
    1370

<210> SEQ ID NO 6
<211> LENGTH: 54
<212> TYPE: DNA
<213> ORGANISM: Artificial Sequence
<220> FEATURE:
<223> OTHER INFORMATION: Native leader

<400> SEQUENCE: 6
atgaaatcac tcacttactt ctggctgttt ctccccgtgc tctcaaccct ctct         54

<210> SEQ ID NO 7
<211> LENGTH: 18
<212> TYPE: PRT
<213> ORGANISM: Artificial Sequence
<220> FEATURE:
<223> OTHER INFORMATION: Native leader

<400> SEQUENCE: 7

Met Lys Ser Leu Thr Tyr Phe Trp Leu Phe Leu Pro Val Leu Ser Thr
1               5                   10                  15

Leu Ser

<210> SEQ ID NO 8
<211> LENGTH: 54
<212> TYPE: DNA
<213> ORGANISM: Artificial Sequence
<220> FEATURE:
<223> OTHER INFORMATION: IgE leader

<400> SEQUENCE: 8
atggactgga cttggattct gtttctggtg gccgctgcta cccgagtgca ttct         54

<210> SEQ ID NO 9
<211> LENGTH: 18
<212> TYPE: PRT
<213> ORGANISM: Artificial Sequence
<220> FEATURE:
<223> OTHER INFORMATION: IgE leader
```

```
<400> SEQUENCE: 9

Met Asp Trp Thr Trp Ile Leu Phe Leu Val Ala Ala Ala Thr Arg Val
1               5                   10                  15

His Ser
```